(12) United States Patent
Sikes et al.

(10) Patent No.: US 8,652,506 B2
(45) Date of Patent: Feb. 18, 2014

(54) BIO-DEGRADABLE BLOCK CO-POLYMERS FOR CONTROLLED RELEASE

(75) Inventors: Courtney Sikes, Uxbridge, MA (US); Mark Boden, Harrisville, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1362 days.

(21) Appl. No.: 12/133,728

(22) Filed: Jun. 5, 2008

(65) Prior Publication Data

US 2009/0304767 A1 Dec. 10, 2009

(51) Int. Cl.
*A61F 2/00* (2006.01)
*C08G 63/08* (2006.01)
*A61K 47/34* (2006.01)

(52) U.S. Cl.
USPC ......... 424/426; 424/423; 525/411; 514/772.7

(58) Field of Classification Search
None
See application file for complete search history.

(56) References Cited

U.S. PATENT DOCUMENTS

| | | | |
|---|---|---|---|
| 5,928,940 A | 7/1999 | Sampath et al. | |
| 6,004,573 A | 12/1999 | Rathi et al. | |
| 6,099,562 A | 8/2000 | Ding et al. | |
| 6,117,949 A | 9/2000 | Rathi et al. | |
| 6,153,252 A | 11/2000 | Hossainy et al. | |
| 6,201,072 B1 | 3/2001 | Rathi et al. | |
| 6,238,121 B1 | 5/2001 | Roser | |
| 6,258,121 B1 | 7/2001 | Yang et al. | |
| 6,277,927 B1 * | 8/2001 | Roby et al. | 525/411 |
| 6,326,021 B1 | 12/2001 | Schwendeman et al. | |
| 6,451,346 B1 | 9/2002 | Shah et al. | |
| 6,541,033 B1 | 4/2003 | Shah | |
| 6,569,195 B2 | 5/2003 | Yang et al. | |
| 6,592,899 B2 | 7/2003 | Fowers et al. | |
| 6,890,560 B2 | 5/2005 | Seo et al. | |
| 6,986,899 B2 | 1/2006 | Hossainy et al. | |
| 7,179,289 B2 | 2/2007 | Shanley | |
| 7,179,867 B2 | 2/2007 | Chang et al. | |
| 7,226,616 B2 | 6/2007 | Seo et al. | |
| 7,247,364 B2 | 7/2007 | Hossainy et al. | |
| 7,311,901 B2 | 12/2007 | Seo et al. | |
| 7,311,980 B1 | 12/2007 | Hossainy et al. | |
| 2003/0017206 A1 | 1/2003 | Seo et al. | |
| 2003/0031911 A1 | 2/2003 | Ritts et al. | |
| 2003/0049511 A1 | 3/2003 | Ritts et al. | |
| 2003/0068377 A1 | 4/2003 | Fowers et al. | |
| 2003/0099709 A1 | 5/2003 | Shah et al. | |
| 2003/0113606 A1 | 6/2003 | Ritts et al. | |
| 2003/0228366 A1 | 12/2003 | Shih et al. | |
| 2003/0228681 A1 | 12/2003 | Ritts et al. | |
| 2004/0142014 A1 | 7/2004 | Litvack et al. | |
| 2004/0143321 A1 | 7/2004 | Litvack et al. | |
| 2004/0143322 A1 | 7/2004 | Litvack et al. | |
| 2004/0202692 A1 | 10/2004 | Shanley et al. | |
| 2004/0204756 A1 | 10/2004 | Diaz et al. | |
| 2004/0219175 A1 | 11/2004 | Kan et al. | |
| 2004/0219214 A1 | 11/2004 | Gravett et al. | |
| 2004/0220660 A1 | 11/2004 | Shanley et al. | |
| 2004/0225350 A1 | 11/2004 | Shanley | |
| 2004/0234494 A1 | 11/2004 | Seo et al. | |
| 2004/0253195 A1 | 12/2004 | Seo et al. | |
| 2005/0010170 A1 | 1/2005 | Shanley et al. | |
| 2005/0073075 A1 | 4/2005 | Chu et al. | |
| 2005/0100577 A1 | 5/2005 | Parker et al. | |
| 2005/0106257 A1 | 5/2005 | Albayrak | |
| 2005/0112170 A1 | 5/2005 | Hossainy et al. | |
| 2005/0113531 A1 | 5/2005 | Chang et al. | |
| 2005/0182390 A1 | 8/2005 | Shanley | |
| 2005/0201972 A1 | 9/2005 | Seo et al. | |
| 2005/0234538 A1 | 10/2005 | Litvack et al. | |
| 2005/0271697 A1 | 12/2005 | Litvack | |
| 2005/0271726 A1 | 12/2005 | Crum | |
| 2005/0287287 A1 | 12/2005 | Parker et al. | |
| 2006/0002975 A1 | 1/2006 | Litvack et al. | |
| 2006/0018872 A1 | 1/2006 | Tew et al. | |
| 2006/0034889 A1 | 2/2006 | Jo et al. | |
| 2006/0040894 A1 | 2/2006 | Hunter et al. | |
| 2006/0067927 A1 | 3/2006 | Chandrasekaran et al. | |
| 2006/0069168 A1 | 3/2006 | Tabata et al. | |
| 2006/0122697 A1 | 6/2006 | Shanley et al. | |
| 2006/0142541 A1 * | 6/2006 | Hossainy | 528/354 |
| 2006/0147489 A1 | 7/2006 | Shanley et al. | |
| 2006/0154126 A1 | 7/2006 | Ritts et al. | |
| 2006/0178734 A1 | 8/2006 | Parker et al. | |

(Continued)

FOREIGN PATENT DOCUMENTS

| DE | 2849785 | 5/1979 |
|---|---|---|
| WO | 0214403 | 2/2002 |
| WO | 2006071860 | 7/2006 |

OTHER PUBLICATIONS

International Search Report for Application No. PCT/US2009/046285 filed on Jun. 4, 2009.

*Primary Examiner* — Bethany Barham
*Assistant Examiner* — Danah Al-Awadi
(74) *Attorney, Agent, or Firm* — Vidas, Arrett & Steinkraus, P.A.

(57) ABSTRACT

A block or graft copolymer includes a first block, and a second block different from the first block, wherein the first block is a poly(lactide-glycolide) copolymer. The polymers may be formulated in compositions with drug components for use in coating medical devices such as stents. Different blocks of the block or graft copolymer degrade in the body at different rates. The drug release profile from the coating is a combination the individual release rates of the different blocks and so can be controlled by controlling the selection and relative amounts of the respective blocks.

11 Claims, No Drawings

(56) References Cited

U.S. PATENT DOCUMENTS

| | | |
|---|---|---|
| 2006/0178735 A1 | 8/2006 | Litvack et al. |
| 2006/0204546 A1 | 9/2006 | Nguyen et al. |
| 2006/0204547 A1 | 9/2006 | Nguyen et al. |
| 2006/0229713 A1 | 10/2006 | Shanley et al. |
| 2006/0253068 A1 | 11/2006 | Van Bilsen et al. |
| 2007/0065477 A1 | 3/2007 | Parker et al. |
| 2007/0110788 A1 | 5/2007 | Hissong et al. |
| 2007/0112414 A1 | 5/2007 | Parker et al. |
| 2007/0116697 A1 | 5/2007 | Osterhout et al. |
| 2007/0172509 A1 | 7/2007 | Nguyen et al. |
| 2007/0191935 A1 | 8/2007 | Parker et al. |
| 2007/0259020 A1 | 11/2007 | Langer et al. |
| 2007/0259047 A1 | 11/2007 | Ogawa et al. |
| 2007/0265356 A1 | 11/2007 | Kim et al. |
| 2007/0269486 A1 | 11/2007 | Parker et al. |
| 2008/0015494 A1 | 1/2008 | Santini et al. |
| 2008/0033260 A1 | 2/2008 | Sheppard et al. |
| 2008/0124400 A1 | 5/2008 | Liggins et al. |
| 2008/0152616 A1 | 6/2008 | Seo et al. |
| 2008/0188925 A1 | 8/2008 | Zhao |
| 2008/0234800 A1 | 9/2008 | Clarke |
| 2008/0234831 A1 | 9/2008 | Clarke et al. |
| 2008/0248098 A1 | 10/2008 | Jin et al. |
| 2008/0248122 A1 | 10/2008 | Rashba-Step et al. |
| 2008/0248126 A1 | 10/2008 | Cheng et al. |
| 2008/0260850 A1 | 10/2008 | Yi et al. |
| 2008/0311040 A1 | 12/2008 | Berry et al. |
| 2009/0047322 A1* | 2/2009 | Vange et al. .............. 424/423 |
| 2009/0110711 A1* | 4/2009 | Trollsas et al. ............ 424/423 |

* cited by examiner

BIO-DEGRADABLE BLOCK CO-POLYMERS FOR CONTROLLED RELEASE

FIELD OF THE INVENTION

The present invention relates to the field of controlled, local delivery of pharmacologically active agents, to polymer compositions useful therein, and to methods of making and using such polymer compositions.

BACKGROUND OF THE INVENTION

Systemic administration of drugs for the treatment of diseases can be effective, but may not be the most efficacious method for diseases which are localized within specific parts of the body. The controlled localized delivery of a drug to diseased tissue has become increasingly desirable because local administration of drugs can produce fewer side effects, and effective amounts of the drug will usually be smaller so the drug expense can be reduced.

Controlled localized delivery in body lumens can be difficult because the movement of bodily fluids through body lumens such as blood vessels and ducts can carry the drug away from the afflicted area.

Some methods of controlled local delivery of drugs involve inserting or implanting medical devices that include a polymer composition for release of a biologically active material. These polymer compositions may be applied to the surface as a coating. For example, various types of drug-coated stents have been used for localized delivery of drugs to a body lumen. An example is provided in U.S. Pat. No. 6,099,562 to Ding et al, and U.S. Pat. No. 6,238,121 to Yang et al. Such stents have been used to prevent, inter alia, the occurrence of restenosis after balloon angioplasty.

In at least some systems drug delivery is provided largely as a polymer coating degrades. This has the advantage that delivery profile over time should be a function of the polymer degradation rate. However, in practice it has been difficult to match a polymer degradation rate to a desired drug delivery profile.

SUMMARY OF THE INVENTION

In some aspects the present invention pertains to novel block or graft copolymers which include at least a first block and a second block different from the first block wherein the first block is a poly(lactide-glycolide) ("PLGA") copolymer.

In other aspects the present invention pertains to novel compositions comprising a polymer and a drug component in which the polymer is a block or graft copolymer containing at least a poly(lactide-glycolide) (PLGA) block and at least a second polymer block of a polymer degradable at a slower rate than the (PLGA) block.

The polymers may be formulated in compositions which also include a drug component. The compositions may be used to form drug eluting coatings for medical devices such as stents. Different blocks of the block or graft copolymer degrade in the body at different rates. The release profile from such a coating is a combination the individual release rates of the different blocks and so can be controlled by controlling the selection and relative amounts of the respective blocks.

Still further aspects pertain to medical devices such as stents which employ a coating of a drug eluting coating formed of a composition of the invention.

These and other aspects of the invention will be apparent to the skilled person from the disclosure herein.

DETAILED DESCRIPTION OF THE INVENTION

As used herein "block-copolymer" refers to a copolymer containing a linear arrangement of blocks. "Graft copolymer" refers to a polymer composed of macromolecules with one or more blocks connected to a polymer main chain as side chains. In some cases non-polymeric groups, that is groups that are not themselves part of a sequentially repeating structure, may be used to join the blocks of the block or graft copolymers of the invention. For purposes of the present invention, the collective term "block or graft copolymer" should also be taken to include star polymers which have multiple different polymer blocks radiating from a central moiety that is not necessarily polymeric and also taken to include polymers that have two or more linearly arranged blocks and one or more side chains. A block is defined as a portion of a polymer molecule in which the monomeric units have at least one constitutional or configurational feature absent from the adjacent or main chain portions.

A block copolymer of the invention may be a diblock, e.g. AB, a triblock, e.g. ABA, or segmented, e.g. $[AB]_n$ or $[AB]_nA$, where A and B represent the different blocks and n is a number greater than 1, for instance 2-100 or 3-10. A block copolymer of the invention may also comprise more than two different blocks, e.g. ABC, $[AB]_nC$, ABCA, ABCB, ABCB and ABCD, where C and D are additional blocks differing in at least one characteristic way from the A and B blocks. Similarly, in a graft copolymer, two or more blocks may be employed and the side chain blocks may occur as a single branch from a main chain or as multiple branches. Typically the number of repeat units in a block will be greater than 4, for instance about 10 to as much as 100,000 or even more, and the number of blocks in a segmented or graft copolymer will be from about 3 to about 100.

The term "drug," is used herein, unless stated otherwise to be construed broadly, to mean pharmaceutically acceptable substances (i.e., substances that are safe for use in the body) and that have some biological effect on cells of the body, for instance a therapeutic effect. The term also includes substances that are being tested for safety for use in the body and/or to determine whether (or what) biological effect they have on cells of the body. The subject body may be a human or other mammal. General and specific examples provided herein are intended to be illustrative of compounds and materials included in the term "drugs" according to the present invention and non-limiting of the scope of the term.

Examples of drugs that may be used in the present invention include steroidal and nonsteroidal anti-inflammatory, antiproliferative, antineoplastic, antimitotic, antiplatelet, antifibrin, antithrombin, antibiotic, anticoagulant, antioxidant, and antiallergic substances, histone deacetylase (HDAC) inhibitors, smooth muscle cell inhibitors, growth factors, growth factor inhibitors, cell adhesion inhibitors, cell adhesion promoters, agents that enhance the formation of healthy neointimal tissue, including endothelial cell regeneration, and combinations thereof. Further examples are known in the art and include the compounds listed in US 2005/0112170 A1 at [0079]. Examples of types of molecules that may be drugs include proteins and peptides, small molecules, antibodies, multi-cyclical molecules, macrolides, nucleic acids, and the like.

In some embodiments the drug is a restonosis-inhibiting drug. Examples of restonosis-inhibiting drugs that may be used in the present invention include anticoagulant agents, antiproliferative agents, antimigratory agents, antimetabolic agents, anti-inflammatory agents, and immunosuppressive substances, and combinations thereof. Particularly useful restenosis-inhibiting drugs include paclitaxel, rapamycin (also known as sirolimus), everolimus, tacrolimus, dexamethoasone, estradiol, ABT-578 (Abbott Laboratories), trapidil, liprostin, Actinomycin D, Resten-NG, Ap-17, clopidogrel and Ridogrel.

In some embodiments the invention pertains to drug eluting stent coatings in which the stent is coated with a restenosis-inhibiting drug that is a microtubule stabilizing agent such as Taxol, paclitaxel, analogues, derivatives, and mixtures thereof. Derivatives believed suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Combinations of different drugs may be used. In some cases it may be desirable to include two or more drugs that have additive, or even synergistic effects. In such cases it will usually be desirable to utilize drugs that will not interfere with, degrade, destabilize, or otherwise interfere with one another. However, in some cases in may be desirable to include a first drug along with a second drug that reduces or alters the activity of the first drug in a particular manner. The many possible permutations allow for great flexibility in treatment.

The "drug component," i.e. the drug or combination of drugs employed in the invention, is employed in a coating composition together with a polymer that serves to elute the drug over time as the polymer degrades. The invention has particular advantage to drugs that release from lactide polymers such as lactide/glycolide copolymers.

The release of drugs from formulations with lactide-glycolide copolymer (PLGA) may be governed to a large extent by the degradation of the polymer. This is especially true for compositions using low drug percentages and polymers within the lactide-glycolide copolymer family with higher mole fractions of lactide. As polymers in this family increase in mole fraction of lactide, this period of maximally dynamic degradation is delayed. Drug release follows a lag time prior to degradation that increases with increasing lactide content.

For instance when a stent having a thin coating (e.g. 200 µg total coat weight) of 95 weight % lactide-glycolide random copolymer polymer (85:15 ratio of lactide to glycolide units) and 5 weight % drug (paclitaxel) is implanted, the drug is released as the polymer degrades. However, the release profile is not linear. As the polymer degrades the barrier to drug release is significantly reduced. The drug elutes from the coating at increasing rates correlating with the increased polymer degradation that occurs as the time period from implantation increases. Consequently with this polymer the greater portion of the drug is delivered at the later stages of the polymer degradation. Controlled delivery of paclitaxel can be achieved with lower lactide content in the copolymer (example: PLGA 50:50), but due to the short time that this polymer takes to degrade in the body the duration of drug delivery is short for coatings applied to drug eluting stents.

According to the present invention, the release profile is controlled by using degradable block or graft copolymers to deliver the drug. The polymer employed in the present invention is a block or graft copolymer that comprises two or more blocks that elute the drug component at different rates. In some embodiments the polymer has at least one first block of a poly(lactide-glycolide) copolymer that elutes the drug component at a first rate and a second block that elutes the drug at a second, slower rate. It should be noted that the characterization of the "first" and "second" blocks here does not indicate a location or orientation within the polymer. For instance either the first block or the may be an end block, a mid-block, a side chain block, or may have some other orientation within the block or graft copolymer structure.

Since the polymer blocks degrade at different rates, the drug release from the respective blocks will release the drug component at different rates. Thus the release profile from such a coating will be a combination the individual release rates of the different blocks. This allows for a coating to be designed with an extended time release profile while reducing or eliminating the dynamic release profile obtained when a single slow release polymer is employed. In this regard in some embodiments it may be desirable for the respective polymer blocks to be sufficiently different that micro domain phase separation occurs.

In some embodiments the second block is a random lactide-glycolide copolymer having a higher percentage of lactide than the first block copolymer. In other embodiments the second block is a polylactide homopolymer (PLA). PLA includes poly(D,L-lactic acid) (DLPLA), poly(D-lactic acid), poly(L-lactic acid) or any combination thereof. In still other embodiments the second block is poly(trimethylene carbonate), poly(caprolactone), poly(β-butyrolactone), poly(δ-valerolactone), or poly(tyrosine carbonate). In some embodiments a three or more different blocks having different elution profiles may be employed.

In some embodiments the drug component and polymer composition form a coating in which the drug is distributed essentially uniform throughout the coating but releases from different microdomains at different rates because those domains degrade at different rates. In some embodiments each different block of the block copolymer is hydrophobic and/or solid at body temperature ($t_m > 37°$ C.). In at least some embodiments the block copolymer is a non-crosslinked thermoplastic material.

Examples of polymers usable in the invention include an AB, ABA, BAB, $[AB]_n$, $[AB]_nA$ or $[BA]_nB$ block copolymer in which A is a PLGA block that has relatively low content of lactide units (e.g. 25:75 to 60:40 lactide:glycolide ratio) and B is PLGA block that has a higher lactide content (e.g. lactide: glycolide ratios of 70:30 to 99:1), a PLA block, or a poly (caprolactone), poly(hydroxybutyrate), poly(hydroxyvalerate), poly(trimethylene carbonate) or poly(tyrosine carbonate) block. The molecular weight of blocks A and B can be between about 300 and about 100,000 Daltons or even higher, for instance about 5,000 to about 50,000 Daltons.

An example of a triblock copolymer that may be employed is an ABC block, in which A is a 50:50 PLGA copolymer, B is a random PLGA copolymer block that has a higher lactide content, for instance 85:15 glycolide:lactide units, and C is a lactide homopolymer or a poly(trimethylene carbonate), poly (caprolactone), poly(β-butyrolactone), poly(δ-valerolactone), or poly(tyrosine carbonate).

The drug elution profile of the composition will also be a function of by the relative amounts of the blocks within the block copolymer. As a consequence even closer modification of an elution profile toward a desired objective can be provided by altering the relative number or relative size of the respective blocks. For instance on a 100% weight basis, the first block may constitute from about 5% to about 95% of the polymer the second block may constitute from about 5% to about 95% of the polymer, and the third block, if present may constitute from about 1% to about 90% of the polymer. In some cases the first block may constitute 20-80%, or 25-75%, of the polymer; the second block may constitute 20%-80%, or 25-75%, of the polymer; and the third block, if present may constitute 3%-60%, or 5%-40% of the polymer.

The drug may be dissolved in, suspended in, conjugated with (i.e. covalently linked to), or ionically linked to the block copolymer. The composition may be prepared, for instance by absorbing the drug onto the block copolymer; mixing the drug and the block copolymer; reacting the drug and block copolymer, optionally using an intermediate linking structure; forming the block copolymer in the presence of a drug or drug derivative; casting the composition from a common solvent or dispersion, or any other suitable means or combination thereof that allows the drug to be released over time.

The coating may be formed in any conventional way, for instance by dissolving the polymer and drug in a solvent or mixture of solvents and applying the composition to the stent by any suitable technique, such as spraying, dipping, brushing, etc, and allowing the solvent to dry. Alternatively a suspension of both of the components may be disbursed in a liquid vehicle such as water and similarly applied. In some cases a vehicle may act as a solvent for one component, whereas the other may be dispersed in the vehicle, the resulting mixture being applied to the stent similarly. Extrusion of the coating or of a paste comprising the coating and a liquid vehicle may be a suitable application technique in some instances. In some cases the coating may be annealed at a temperature above body temp for a period of time to improve or stabilize the film quality or drug distribution.

In the coating composition, on a dry weight basis, the drug component will typically be from about 0.1 to about 40% of the composition weight, for instance about 0.5 to about 20% or about 1 to about 10%. The block or graft copolymer of the invention is typically the major component of the composition and may make up the balance thereof. In some cases other additives may be included in the composition. Additives may be employed for instance to affect the film forming properties of the composition, to compatibilize the drug with the polymer, or for other purposes.

The polymeric coating of the present invention can be used with various stents. A particular use for the coating is for coronary stents. The stents can be used following angioplasty to inhibit restenosis. The stent body can serve to hold the vessel open against any restenosis and to deliver the restenosis-inhibiting agent. In one embodiment, the coating is substantially continuous over the stent body. In another embodiment, the coating is applied to selected areas of the stent. The coating can be applied directly to the base material of the stent, which may be metal, polymer or ceramic. In some cases it may be desirable to utilize an intervening coating layer between the stent material and the drug-polymer coating. An intervening layer may be employed, for instance, to improve adhesion of the polymer/drug layer or if it is desired that the stent have a permanent non-degradable coating that remains on the stent after degradation of the drug/polymer layer.

In use, a stent according to the present invention can be selected according to desired release dosage profile and provided to the treating physician. After an angioplasty procedure, the coated stent having a restenosis-inhibiting drug in the coating can be delivered to the stenosed, recently dilated coronary artery region. Delivery can be accomplished using methods well known to those skilled in the art, such as mounting the stent on an inflatable balloon disposed at the distal end of a catheter. With the stent advanced into position near the dilated region, the stent can be forced outward and into position against the inner vessel walls. If the stent is self-expanding, the stent can be delivered by deploying the stent from within a delivery device, allowing the stent to expand against the inner vessel walls. Over time, the polymeric coating is eroded by bodily fluids. The drug, as it is released from the eroding polymeric coating, can be absorbed by the inner vessel walls.

While the coatings of the present invention have been described with particular reference to coronary stents, they can also be used with a variety of other implantable prostheses and other implantable medical devices. Examples of the implantable medical devices that can be used in conjunction with the embodiments of this invention include sutures, pumps, stent-grafts, grafts (e.g., aortic grafts), heart valves, shunts, vascular access ports, pacemakers, defibrillators, electrodes, and leads. The present invention may be used with other types of implantable prostheses not specifically mentioned herein. The coated device may be one that, other than the inventive coating, is designed to remain stable in the body indefinitely or it may be one that itself degrades or becomes integrated with body tissue over time.

All published documents, including all U.S. patent documents, mentioned anywhere in this application are hereby expressly incorporated herein by reference in their entirety. Any copending patent applications, mentioned anywhere in this application are also hereby expressly incorporated herein by reference in their entirety.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. An implantable medical device having a coating thereon wherein the coating comprises a block or graft copolymer that comprises at least a first block, a second block different from the first block, and a third block, wherein the first block is a poly(lactide-glycolide) copolymer, the second block is a member of the group consisting of lactide-glycolide copolymer having a higher percentage of lactide than the first block copolymer, polylactide homopolymer, poly(trimethylene carbonate), poly(caprolactone), poly(β-butyrolactone), poly(δ-valerolactone), and poly(tyrosine carbonate), the first and second blocks are characterized by respective degradation rates when the block copolymer is placed in the body of a subject animal, the degradation rate of the first block being greater than the degradation rate of the second block, and the third block being characterized by a degradation rate when the block copolymer is placed in the body of a subject animal that is different from the respective degradation rates of the first and second blocks.

2. An implantable medical device as in claim 1 wherein said coating is a composition comprising said block or graft copolymer and a drug component distributed in said block or graft copolymer.

3. An implantable medical device as in claim 1 wherein the device is a member of the group consisting of sutures, pumps, stents, stent-grafts, grafts, heart valves, shunts, vascular access ports, pacemakers, defibrillators, electrodes, and leads.

4. An implantable medical device as in claim 2 wherein the device is a stent.

5. A stent as in claim 4 wherein the drug component comprises a restenosis-inhibiting drug.

6. A stent as in claim 4 wherein the drug component comprises at least one member of the group consisting of paclitaxel, derivatives of paclitaxel, rapamycin, everolimus, tacrolimus, dexamethoasone, estradiol, ABT-578 (Abbott Laboratories), trapidil, liprostin, Actinomycin D, Resten-NG, Ap-17, clopidogrel, and Ridogrel.

7. An implantable medical device as in claim 1 wherein:
the second block of said block or graft copolymer is a member of the group consisting of lactide-glycolide copolymer having a higher percentage of lactide than the first block copolymer, polylactide homopolymer, poly(trimethylene carbonate), poly(caprolactone), poly(β-butyrolactone), poly(δ-valerolactone), and poly(tyrosine carbonate), or
each different block of the block copolymer is hydrophobic.

8. An implantable medical device as in claim 1 wherein the second block of said block copolymer is a lactide-glycolide copolymer having a higher percentage of lactide than the first block copolymer.

9. An implantable medical device as in claim 8 wherein the third block of said block copolymer is selected from the group consisting of polylactide homopolymer, poly(caprolactone), poly(hydroxybutyrate), poly(hydroxyvalerate), poly(trimethylene carbonate) and poly(tyrosine carbonate).

10. An implantable medical device as in claim 2 wherein the drug component comprises a restenosis-inhibiting drug.

11. A stent as in claim 2 wherein the drug component comprises at least one member of the group consisting of paclitaxel, derivatives of paclitaxel, rapamycin, everolimus, tacrolimus, dexamethoasone, estradiol, ABT-578 (Abbott Laboratories), trapidil, liprostin, Actinomycin D, Resten-NG, Ap-17, clopidogrel, and Ridogrel.

* * * * *